(12) United States Patent
Hickey et al.

(10) Patent No.: US 9,518,237 B2
(45) Date of Patent: Dec. 13, 2016

(54) INTEGRATED PROCESSES FOR REFINING SYNGAS AND BIOCONVERSION TO OXYGENATED ORGANIC COMPOUND

(71) Applicant: Coskata, Inc., Warrenville, IL (US)

(72) Inventors: Robert Hickey, Okemos, MI (US); Jianxin Du, Naperville, IL (US)

(73) Assignee: Synata Bio, Inc., Warrenville, IL (US)

( * ) Notice: Subject to any disclaimer, the term of this patent is extended or adjusted under 35 U.S.C. 154(b) by 91 days.

(21) Appl. No.: 14/645,169

(22) Filed: Mar. 11, 2015

(65) Prior Publication Data

US 2015/0184093 A1 Jul. 2, 2015

Related U.S. Application Data

(62) Division of application No. 13/440,953, filed on Apr. 5, 2012, now Pat. No. 9,011,578.

(51) Int. Cl.
*C10J 3/72* (2006.01)
*C10K 1/00* (2006.01)
(Continued)

(52) U.S. Cl.
CPC .. *C10K 1/10* (2013.01); *C10J 3/72* (2013.01); *C10K 1/002* (2013.01); *C10K 1/005* (2013.01); *C10K 1/046* (2013.01); *C12P 7/065* (2013.01); *C12P 7/08* (2013.01); *C12P 7/16* (2013.01); *C10G 2300/1011* (2013.01); *C10J 2300/093* (2013.01); *C10J 2300/0916* (2013.01); *C10J 2300/0943* (2013.01); *C10J 2300/0946* (2013.01); *C10J 2300/0959* (2013.01); *C10J 2300/0976* (2013.01);
(Continued)

(58) Field of Classification Search
CPC ............... C10G 2300/1011; C10G 2300/0916; C10G 2300/093; C10G 2300/0943; C10G 2300/0946; C10G 2300/0959; C10G 2300/0976; C10G 2300/1603; C10G 2300/1615; C10G 2300/1618; C10G 2300/1846; C10G 2300/1853; C10J 3/72; C10K 1/002; C10K 1/005; C10K 1/046; C10K 1/10; C12P 7/065; C12P 7/08; C12P 7/16; Y02E 50/10; Y02E 50/17; Y02P 20/125; Y02P 20/582
See application file for complete search history.

(56) References Cited

U.S. PATENT DOCUMENTS

2011/0095234 A1* 4/2011 Hickey .................. C10K 1/102
252/373

* cited by examiner

*Primary Examiner* — Duane Smith
*Assistant Examiner* — Cabrena Holecek
(74) *Attorney, Agent, or Firm* — Cardinal Law Group

(57) ABSTRACT

Integrated processes are provided for syngas refining and bioconversion of syngas to oxygenated organic compound. In the integrated processes ammonia contained in the syngas is recovered and used as a source of nitrogen and water for the fermentation. The integrated processes first remove tars from syngas by scrubbing using a first aqueous medium under conditions that ammonium bicarbonate is unstable. With tars removed, contact between the syngas and a second aqueous medium enables ammonia and carbon dioxide to be removed from the syngas without undue removal of components adverse to the fermentation, processing or oxygenated product such as benzene, toluene, xylene, ethylene, acetylene, and hydrogen cyanide. At least a portion of the second aqueous medium is supplied as a source of water and ammonia for the fermentation.

12 Claims, 1 Drawing Sheet

(51) Int. Cl.
*C10K 1/04* (2006.01)
*C10K 1/10* (2006.01)
*C12P 7/16* (2006.01)
*C12P 7/06* (2006.01)
*C12P 7/08* (2006.01)

(52) U.S. Cl.
CPC ............ *C10J 2300/1603* (2013.01); *C10J 2300/1615* (2013.01); *C10J 2300/1618* (2013.01); *C10J 2300/1846* (2013.01); *C10J 2300/1853* (2013.01); *Y02E 50/10* (2013.01); *Y02E 50/17* (2013.01); *Y02P 20/125* (2015.11); *Y02P 20/582* (2015.11)

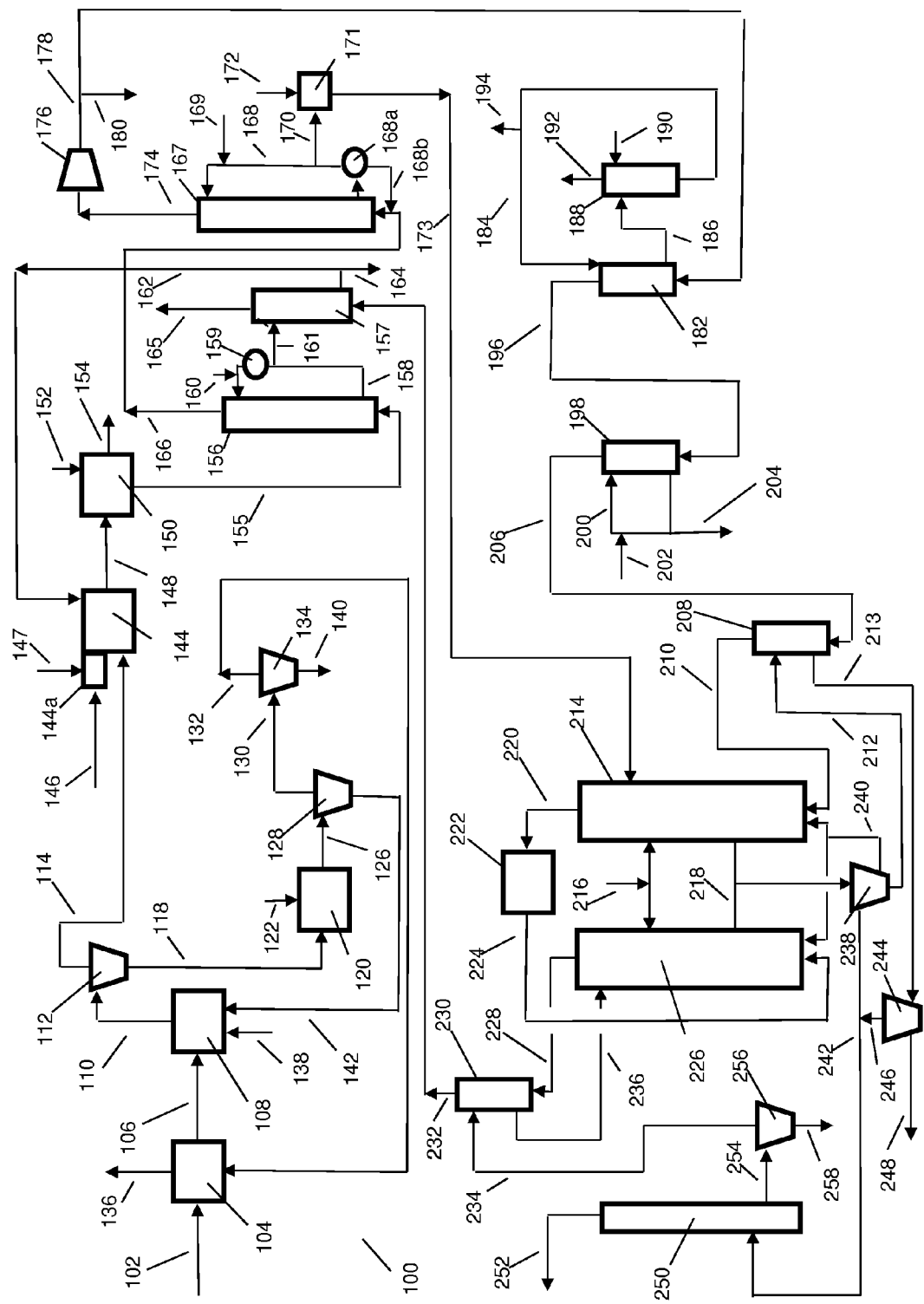

INTEGRATED PROCESSES FOR REFINING SYNGAS AND BIOCONVERSION TO OXYGENATED ORGANIC COMPOUND

CROSS-REFERENCE TO RELATED APPLICATIONS

The present application is a divisional application of U.S. patent Ser. No. 13/440,953, filed Apr. 5, 2012, incorporated herein in its entirety by reference.

FIELD OF THE INVENTION

This invention pertains to integrated processes for refining syngas and its bioconversion to oxygenated organic compound in a commercially attractive manner.

BACKGROUND

For purposes herein, synthesis gas (syngas) is a gas containing carbon monoxide and frequently hydrogen, although term "syngas", for purposes herein, is also intended to encompass carbon monoxide gas streams that may have little or no hydrogen. Typically, carbon monoxide is present in an amount of at least about 20 volume percent, and the syngas typically contains other components in addition to hydrogen such as carbon dioxide, nitrogen and water vapor. Syngas may derived from various sources, including, but not limited to, gasification of carbonaceous feedstocks such as biomass, landfill gas, coal, natural gas, and petroleum; coke oven gas and gas from other industrial operations such as petroleum refining and steel mill waste gas.

Anaerobic fermentations of carbon monoxide and hydrogen and carbon dioxide have also been proposed and involve the contact of the substrate gas in a liquid, aqueous menstruum with microorganisms capable of generating oxygenated organic compounds such as ethanol, acetic acid, n-propanol and n-butanol. For instance, the theoretical equations for the conversion of carbon monoxide and hydrogen to ethanol are:

$$6CO + 3H_2O \cdot C_2H_5OH + 4CO_2$$

$$6H_2 + 2CO_2 \cdot C_2H_5OH + 3H_2O.$$

As can be seen, the conversion of carbon monoxide results in the generation of carbon dioxide. The conversion of hydrogen involves the consumption of hydrogen and carbon dioxide, and this conversion is sometimes referred to as the $H_2/CO_2$ conversion.

Syngas typically contains components other than carbon monoxide, hydrogen, carbon dioxide, nitrogen, and water vapor. Some of these components such as ammonia, carbonyl sulfide and hydrogen sulfide can be tolerated by the microorganisms, and some may even be able to serve as nutrients or additives useful to the microorganisms. However, some of these components such as tars, benzene, toluene, xylene, ethylene, acetylene, hydrogen cyanide and nitric oxide are typically contained in syngas at concentrations that pose undesirable effects on the microorganism, processing equipment and product quality. For example, tars, which are naphthalene and heavier aromatic compounds, become solid at temperatures used for anaerobic fermentation, and the solids can build-up resulting in operational problems with piping, pumps, instrument probes and valves. Accordingly, the syngas must be subjected to a clean-up (refining) operation to make it suitable for supplying substrate to anaerobic fermentations.

A desire exists to use syngas efficiently both in the fermentation operation to make higher value products and in conserving the syngas values in any cleanup operation. In addition to capital and operating costs for effecting syngas clean-up, consideration must be given to the costs for safe and environmentally acceptable disposal of the removed contaminants. For a syngas to oxygenated organic compound fermentation process to be commercially viable, capital and operating costs must be sufficiently low that it is at least competitive with alternative biomass to oxygenated organic compound processes. For instance, ethanol is currently commercially produced from corn and cane sugar in facilities having name plate capacities of over 100 million gallons per year at sufficiently low costs to be competitive with fossil fuels. Biomass to syngas to oxygenated organic compound fermentation processes face even greater challenges due to the multiple major operations required to convert the biomass to syngas, to cleanup the syngas sufficiently to be used in an anaerobic fermentation, to effect the anaerobic fermentation and then to recover a merchantable product. Moreover, conservation of nutrients, adjuvants and resources such as water is important to provide a commercially attractive process.

Processes are therefore sought to refine and then bioconvert syngas to oxygenated organic compound at low capital and operating costs.

SUMMARY OF THE INVENTION

In accordance with this invention processes are provided for integrated syngas refining and bioconversion of syngas to oxygenated organic compound. The integrated processes of this invention permit ammonia contained in the syngas to be recovered and introduced into the aqueous menstruum, often without further purification. The integrated processes of this invention can also provide for the recovery of water from the syngas that has a sufficient absence of components that can be adverse to the microorganisms, processing equipment and oxygenated organic product, that it can be introduced into the aqueous menstruum or otherwise used as process water in the syngas in the process or in the process for producing the syngas. An advantage of recovering water from the syngas is that the water has a substantial absence of molecular and free-oxygen-containing moieties as is required for anaerobic fermentation processes. The integrated processes of this invention further reduce the demand on waste water treatment and reduce the amount of hazardous waste. The processes of this invention can thus reduce capital and operating costs of a syngas to oxygenated organic product production facility, and especially facilities that include a biomass to syngas operation.

In the broad aspects of the invention, integrated processes are provided for refining a syngas containing tars (naphthalene and high molecular weight compounds), ammonia, hydrogen cyanide, benzene, toluene, xylene, methane, ethylene and acetylene and bioconverting the refined syngas to oxygenated organic compound comprising:

(a) scrubbing the syngas by contact with a first aqueous medium at a sufficiently high temperature that less than about 40, say, less than about 20, preferably less than about 10, mole percent of the ammonia contained in the syngas is absorbed by the aqueous medium and a pressure sufficient to provide the aqueous medium in the liquid phase to provide a first scrubbed syngas, often at a temperature between about 65° C. and 120° C., preferably between about 70° C. and 100° C., and to provide an aqueous medium containing tars, wherein the contacting is for a duration sufficient such that the first scrubbed syngas contains less than about 5, preferably less than about 1, ppm(mole) naphthalene;

(b) contacting the first scrubbed syngas with a second aqueous medium capable of absorbing ammonia at a temperature at which ammonium bicarbonate is thermally stable to remove at least a portion of the carbon dioxide and at least about 50, preferably at least about 70, say between about 70 and 95, mole percent of the ammonia from the first scrubbed syngas to provide an ammonia-reduced syngas, which syngas is often at a temperature between about 20° C. and 80° C., preferably between about 20° C. and 60° C., and to provide an ammonium bicarbonate-containing aqueous medium, wherein the conditions of the contacting provide the ammonium bicarbonate-containing aqueous medium having a concentration of:
i. benzene less than 1 ppm(mole),
ii. ethylene less than 1 ppm(mole),
iii. acetylene less than 1 ppm(mole) and
iv. hydrogen cyanide less than 1 ppm(mole);

(c) treating the ammonia-reduced syngas to provide a treated syngas containing less than 20 mole percent carbon dioxide, less than 50 ppm(mole) ethylene; less than 5 ppm(mole) acetylene, less than 2 ppm(mole) hydrogen cyanide, said treating often comprising one or more of sorption and chemical treatment;

(d) continuously supplying at least a portion of the treated syngas to a fermentation zone having an aqueous menstruum containing microorganisms suitable for converting syngas to oxygenated organic compound, said aqueous menstruum being maintained under anaerobic fermentation conditions, to produce said oxygenated organic compound; and (e) supplying at least a portion of the ammonium bicarbonate-containing aqueous medium to the fermentation zone.

Advantageously, by maintaining the scrubbing at a high temperature, the aqueous medium in step (a) contains little, if any, other hydrocarbons or components such as ammonia, hydrogen sulfide, carbonyl sulfide, hydrogen cyanide, and lighter hydrocarbons such as methane, ethylene, acetylene, benzene, toluene and xylene. Removal of tars having higher molecular weights than naphthalene (heavy tars) also occurs when naphthalene is removed by scrubbing. In general, these other tars will be more readily removed than naphthalene and will normally be present in the scrubbed syngas in concentrations less than that of naphthalene. The aqueous medium in step (a) will contain ash, when present in the syngas. Generally the aqueous medium is devoid of any appreciable quantity of molecular or reactive oxygen moieties. Hence, the aqueous medium can be useful as process water after removal of any solids, e.g., by centrifugation, filtration, decantation, and the like. Often, the aqueous medium used for the scrubbing in step (a) is maintained at a pH less than about 6.5, say, between about 4.5 or 5 and 6. At these acidities, little ammonium carbonate would be formed. Carbon dioxide that is absorbed by the aqueous medium can frequently result in the desired pH range being obtained.

In a preferred aspect of the invention, at least a portion of the naphthalene and other heavy tars are stripped from the aqueous medium of step (a) after contact with the syngas. Stripping conditions including contact with a stripping gas to reduce the content of naphthalene to less than about 5 ppm(mole). Where the aqueous medium is recycled for further scrubbing per step (a), the stripping may involve the contact with the recirculating aqueous medium or with a purge. Where at least a portion of the aqueous medium containing tars is purged, preferably at least a portion of the aqueous medium used for replacement is aqueous condensate from the syngas. Often, the scrubbing is used to reduce the temperature of the syngas which results in water being condensed from the syngas. In some instances, the temperature of the syngas is reduced during scrubbing by at least about 10° C. or 20° C., say, at least about 50° C., and sometimes between about 70° C. and 100° C.

Any suitable stripping gas may be use to remove tars from the aqueous medium. Advantageously, the stripping gas is obtained from a process off-gas from the process. Preferably, the process off-gas is at least a portion of an off-gas withdrawn from the fermentation zone, most preferably after oxygenated compound has been recovered from the off-gas. This off-gas, which contains unreacted carbon monoxide and, depending upon the source of the syngas, hydrogen, can also contain hydrocarbons. Thus, the spent stripping stream can be, for example, subjected to thermal oxidation to recover heat.

The contact between the scrubbed syngas and the second aqueous medium in step (b) may be conducted in any suitable manner to effect sorption of ammonia in the aqueous medium. Due to the presence of carbon dioxide which is readily soluble in the aqueous medium, ammonium bicarbonate can be formed once the temperature of the contacting is below that at which ammonium bicarbonate is unstable. The contact may be by scrubbing in which the syngas is upwardly passed through a continuous phase of aqueous medium or by contacting the syngas in a continuous phase with droplets of the aqueous medium. Moreover, as the temperature of the syngas exiting step (b) is lower than the temperature of the syngas when it exits step (a), water is condensed from the syngas. The cooling of the syngas may occur at least partially prior to the contacting of step (b) but preferably occurs by direct heat exchange with the aqueous medium. In some instances, step (b) can be a significant source of make-up water to the fermentation process, e.g., at least about 10 percent, say, between about 15 to 30 percent, of the make-up water requirements.

The aqueous medium may be recycled for contact with the scrubbed syngas and a purge taken to maintain constant aqueous medium flow at steady state conditions, and at least a portion of the purge, which contains ammonium bicarbonate, can be supplied to the fermentation zone. The contact may remove a limited amount of other components from the syngas including, but not limited to carbonyl sulfide, hydrogen sulfide and hydrogen cyanide. However, hydrocarbons such as methane, ethylene, acetylene, benzene, toluene and xylene have such limited solubility in the aqueous medium and are generally at relatively low concentrations in the syngas, that the aqueous medium is substantially devoid of these components. Accordingly, the aqueous medium is sometimes suitable for direct introduction into the fermentation zone. Although carbonyl sulfide and hydrogen sulfide can be used or tolerated in the fermentation, hydrogen cyanide has deleterious effects on most microorganisms for the anaerobic conversion of syngas to oxygenated organic compound. Accordingly, where needed, the aqueous stream being passed to the fermentation operation is preferably treated to reduce hydrogen cyanide content. Preferably the treatment is at least one of hydroxyl radical oxidation treatment, adsorption (e.g., onto activated carbon), physical absorption (e.g., with an oxygenated solvent) and biological treatment that does not oxidize or absorb ammonium cation. Frequently it is desired to reduce the hydrogen cyanide content of the aqueous stream being passed to the fermentation to less than about 0.5, more preferably less than about 0.1, ppm(mass).

A particularly desirable use of the processes of this invention pertains to a further integration of the processes with processes for the generation of syngas from carbonaceous feedstock. In this aspect of the invention, integrated process for continuously converting carbonaceous feedstock into oxygenated organic compound comprising:
  (a) continuously gasifying biomass at elevated temperature to provide a syngas at a temperature of at least about 450° C., said syngas containing carbon monoxide, hydrogen, carbon dioxide and water vapor and further containing hydrogen sulfide, carbonyl sulfide, ethylene, acetylene, benzene, toluene, xylene, and tars, ammonia, and hydrogen cyanide;
  (b) cooling the syngas to a temperature between about 85° C. and 200° C.;
  (c) scrubbing the syngas by contact with a first aqueous medium at a temperature sufficiently high temperature that less than 40 percent of the ammonia contained in the syngas is absorbed by the aqueous medium and a pressure sufficient to provide the aqueous medium in the liquid phase to provide a scrubbed syngas and an aqueous medium containing tars, wherein the contacting is for a duration sufficient such that the scrubbed syngas contains less than about 5 ppm(mole) naphthalene;
  (d) contacting the scrubbed syngas with a second aqueous medium capable of absorbing ammonia at a temperature at which ammonium bicarbonate is thermally stable to remove at least a portion of the carbon dioxide and ammonia from the scrubbed syngas to provide an ammonia-reduced syngas and an ammonium bicarbonate-containing aqueous medium having a concentration of:
    i. benzene less than 1 ppm(mole),
    ii. ethylene less than 1 ppm(mole),
    iii. acetylene less than 1 ppm(mole), and
    iv. hydrogen cyanide less than 1 ppm(mole);
  (e) treating the ammonia-reduced syngas to provide a treated syngas containing less than 20 mole percent carbon dioxide, less than 50 ppm(mole) ethylene; less than 5 ppm(mole) acetylene, less than 2 ppm(mole) hydrogen cyanide;
  (f) continuously supplying at least a portion of the treated syngas to a fermentation zone having an aqueous menstruum containing microorganisms suitable for converting syngas to oxygenated organic compound, said aqueous menstruum being maintained under anaerobic fermentation conditions, to produce said oxygenated organic compound; and
  (g) supplying at least a portion of the ammonium bicarbonate-containing aqueous medium to the fermentation zone.

Another aspect of this invention pertains to integrated methods for cooling syngas that is at a temperature above which uncatalyzed water gas shift reactions can occur, e.g., temperatures above about 1000° C., say, above about 1100° C. In accordance with this aspect of the invention, aqueous medium from the scrubbing can be used to very rapidly cool the syngas making use of the latent heat of vaporization without undue water gas shift occurring due to the increased concentration of water in the syngas. Advantageously, the water is maintained in the loop between the cooling of the syngas and the scrubbing to remove tars. Thus the cooling of the syngas can be effected without significant capital or energy expense while conserving water. In further detail, this aspect of the invention comprises:
  (a) continuously gasifying carbonaceous feedstock at a temperature in excess of about 1000° C. to provide a syngas stream containing carbon monoxide, hydrogen, carbon dioxide and water vapor and further containing hydrogen sulfide, carbonyl sulfide, ethylene, acetylene, benzene, toluene, xylene, tars, ammonia, and hydrogen cyanide, the temperature of said syngas stream being sufficiently high that undesired reactions occur;
  (b) cooling the syngas stream to a temperature below the temperature at which uncatalyzed water gas shift can occur;
  (c) scrubbing the syngas said scrubbing by contact with a first aqueous medium at a temperature sufficiently high temperature that less than about 40 percent of the ammonia contained in the syngas is absorbed by the aqueous medium and a pressure sufficient to provide the aqueous medium in the liquid phase to provide a scrubbed syngas and an aqueous medium containing tars, wherein the contacting is for a duration sufficient such that the scrubbed syngas contains less than about 5 ppm(mole) naphthalene;
  (d) contacting the aqueous medium containing tars with stripping gas under stripping conditions sufficient to remove tars from the aqueous medium and provide a lean aqueous medium and a gas containing tars; and
  (e) introducing at least a portion of the lean aqueous medium into the syngas stream of step (b) to cool the syngas by latent heat of vaporization.

BRIEF DESCRIPTION OF THE DRAWINGS

FIG. 1 is a schematic representation of apparatus suitable to carry out the processes of this invention.

DETAILED DISCUSSION

Definitions

The term Component Composition means the composition of a gas where water, nitrogen and any entrained solids have been excluded from the calculation of the concentration of the components. As used herein, unless otherwise stated, compositions of gases are on an anhydrous basis and exclude the presence of nitrogen.

Oxygenated organic compound means one or more organic compounds containing two to six carbon atoms selected from the group of aliphatic carboxylic acids and salts, alkanols and alkoxide salts, and aldehydes. Often oxygenated organic compound is a mixture of organic compounds produced by the microorganisms contained in the aqueous menstruum.

Aqueous menstruum means a liquid water phase which may contain dissolved compounds including, but not limited to hydrogen, carbon monoxide, and carbon dioxide.

Biomass means biological material living or recently living plants and animals and contains at least hydrogen, oxygen and carbon. Biomass typically also contains nitrogen, phosphorus, sulfur, sodium and potassium. The chemical composition of biomass can vary from source to source and even within a source. Sources of biomass include, but are not limited to, harvested plants such as wood, grass clippings and yard waste, switchgrass, corn (including corn stover), hemp, sorghum, sugarcane (including bagasse), and the like; waste such as garbage and municipal solid waste, and gases derived from anaerobic conversion of biomass such as landfill gas and biogas. Biomass does not include fossil fuels such as coal, natural gas, and petroleum.

The abbreviation ppm means parts per million. Unless otherwise stated or clear from the context, ppm for gaseous compositions is on a mole basis (ppm (mole)) and is on a mass basis (ppm(mass)) for liquids and solids.

Stable gas-in-liquid dispersion means a mixture of gas bubbles in liquid where (i) the bubbles predominantly flow in the same direction as the liquid, and (ii) the dispersion is sufficiently stable that it exists throughout the aqueous menstruum, i.e., insufficient coalescing of bubbles occurs to destroy the dispersion.

Overview

The processes of this invention pertain to integrated syngas refining and anaerobic fermentation of the refined syngas to produce oxygenated organic compound.

Syngas

The syngas to be refined in the integrated processes of this invention may be obtained from any suitable source. Often the syngas has a Component Composition containing about 20 to essentially 100 mole percent carbon monoxide, about 0 to 60 mole percent hydrogen, and about 0 to 35, preferably about 3 to 35, mole percent carbon dioxide. Where the syngas is derived from the gasification of carbonaceous feedstock, it typically contains about 20 to 60, preferably between about 30 and 60, mole percent carbon monoxide; about 20 to 60, preferably between about 30 and 60, mole percent hydrogen; and about 3 to 35, say, between about 5 to 25, mole percent carbon dioxide. Often the mole ratio of hydrogen to carbon monoxide is in the range of about 0:1 to 2:1, and for syngas derived from the gasification of carbonaceous feedstock, between about 0.2:1 to 3:1, say, between about 0.4:1 to 1.5:1, and sometimes between about 0.8:1 and 1.3:1 The syngas generally also contains on a Component Composition basis, between about 0.1 and 15 mole percent methane; at least about 20, say, to 10,000 or more, ppm (mole) hydrogen sulfide; at least about 2, sometimes up to 10,000, ppm(mole) benzene, at least about 500, preferably between about 1,000 and 25,000, ppm(mole) ammonia; at least about 10, sometimes at least about 50, say, 10 to 25,000, ppm(mole) ethylene; at least about 1 up to about 2,500 ppm(mole) acetylene; at least about 1, and frequently at least about 10, often at least about 100 to 500, ppm(mole) hydrogen cyanide; and at least about 20, and sometimes at least about 25, say, 30 to 10,000 ppm(mole) naphthalene and other tars. Ash and other particulates such as carryover of fines from any solid media, if used, in the gasification operation.

As stated above, sources of syngas include, but are not limited to, gasification of carbon-containing sources such as biomass, coke oven gas, and gas from other industrial operations such as petroleum refining and steel mill waste gas. Carbonaceous feedstocks for making syngas by pyrolysis or gasification include sources of hydrocarbons such as natural gas, biogas, biomass, especially woody biomass, gas generated by reforming hydrocarbon-containing materials, peat, petroleum coke, coal, waste material such as debris from construction and demolition, municipal solid waste, and landfill gas.

Gasification to generate syngas involves heating carbonaceous feedstock in an oxygen-controlled environment, and for purposes herein includes pyrolysis in the absence of added oxygen. The heat may be provided by direct or indirect heat exchange as stated above. Various types of direct and indirect gasifiers include counter current fixed bed, co-current fixed bed, moving bed, fluidized bed, entrained flow and plasma gasifiers. The gasification may be catalytic, partially catalytic or non-catalytic. Gasifiers may have one or more thermal operations to convert carbonaceous feedstock to syngas. Where two or more thermal operations are used, carbonaceous feedstock may be subjected to a first set of gasification conditions including the presence of controlled amounts of oxidant and then one or both of the solids and gas phases subjected to a further thermal process under a second set of gasification conditions including the presence of controlled amounts of oxidant to convert components to syngas. The oxidant for the thermal processes may be one or more of steam and oxygen. The use of one or more subsequent thermal operations is optional but may be preferred where high conversions of carbonaceous feedstock to syngas are sought. U.S. patent application Ser. No. 13/304,902, filed on Nov. 28, 2011, hereby incorporated by reference in its entirety, discloses partial oxidation processes for treating crude syngas.

The generation of syngas from carbonaceous feedstocks may involve one or more other unit operations such as communition to provide feedstock of suitable size for the gasification process used; drying to provide a desired moisture content (often less than about 30 mass percent, for instance, in the range of about 5 to 20 mass percent); contact with the crude gas stream from the gasifier to heat, and in some instances, initiate pyrolysis of at least a portion of the carbonaceous feedstock; and recover heat from the hot syngas, e.g., to generate steam. Where the syngas contains ash (including char), removal of at least a portion of the solids may be desired. The removal of at least a portion of the solids can be effected in any suitable manner. Cyclones are preferred since in most instances, cyclones are capable of removing sufficient entrained solids.

The syngas produced by gasification is usually at a temperature of at least about 450° C., often between about 500° C. and 1500° C., say, 600° C. to 1250° C. The gasification may be conducted at any suitable pressure including subatmospheric pressure, but is typically conducted at pressures from about 100 to 5000 KPa absolute. An example of a process for gasifying syngas with steam as the oxidant is the Taylor gasification process generally disclosed in United States published patent application No. 2008024496 A1, hereby incorporated by reference in its entirety. Where the syngas is hot, typically heat value in the syngas is recovered in a steam boiler to provide steam supply for the biomass conversion process. Preferably, the steam generated is at a pressure of between about 750 and 1500, say, 900 to 1100, KPa absolute and the temperature of the syngas is reduced to between about 85° C. to 200° C., preferably between about 120° C. and 150° C. Alternatively, or in addition, the syngas may be used in indirect heat exchange with other process streams such as to heat air used to dry biomass.

Scrubbing to Remove Tars

The syngas is subjected to scrubbing with an aqueous medium (the aqueous medium of step (a)) to remove naphthalene and heavy tars. The temperature of the scrubbing is sufficiently elevated such that the amount of ammonia dissolved in the aqueous medium and attenuated as ammonium bicarbonate remains low since ammonia bicarbonate is not stable at these temperatures. The temperature of the scrubbed syngas is preferably between about 65° C. and 120° C., say, between about 70° C. and 100° C. In many instances, the syngas is at a temperature higher than that of the syngas after the scrubbing and direct heat exchange occurs. The direct heat exchange will result in temperature gradients within the scrubbing unit operation. Hence, the exit temperature of the scrubbed syngas is a frequently used measurement to assure that no significant amount of ammonia is sorbed in the aqueous medium. The scrubbing may be conducted at any suitable pressure such that the aqueous medium is below its boiling point. Often the pressure is in the range of from about 50 to 1000 kPa absolute, and frequently in the range of about 80 to 300 kPa absolute. Depending upon the temperature and water content of the syngas, water condensate may be recovered in the scrubbing step.

The scrubbing may be effected using any suitable scrubbing equipment and use any suitable aqueous medium. The scrubbing may be effected by co-current or cross-current contact between the syngas and the aqueous medium. Suitable scrubbers include, but are not limited to, un-packed, trayed and packed columns; spargers; trickle bed contactors; stirred and agitated vessels; vortex scrubbers; venturi scrubbers and tortuous pipe. A plurality of scrubbers may be used in parallel or in series to effect the sought tar reduction in a cost effective manner. If the scrubber employs an aqueous medium as the continuous phase, preferably, the gas phase is in the form of bubbles having sufficiently small diameters to facilitate the recovery of naphthalene and other heavy tars. e.g., bubbles having a diameter of less than about 5, preferably less than about 2, millimeters, preferably between about 20 and 1000, microns. More frequently the gas phase is the continuous phase. The liquid phase may be in the form of small droplets, e.g., having a diameter of less than about 5, preferably less than about 2, millimeters, preferably between about 5 and 1000, microns. In some instances, the aqueous phase may be condensate formed by cooling the syngas in the scrubber by direct or indirect heat exchange.

The aqueous medium for the scrubbing (aqueous medium of step (a)) comprises water and one or more adjuvants can be added to the water. Typically, suitable tar removal can be achieved without using adjuvants. The source of the water may be fresh water or a used process water stream. Condensate from the syngas may be a significant, if not sole, source of the aqueous medium. Where water is condensed from the syngas, a purge stream may be necessary to maintain constant volume at steady state. Water or steam may be added to the syngas prior to the scrubbing to provide desired amounts of condensate.

The duration of the contact between the syngas and the aqueous medium is sufficient to achieve the desired reduction of tars. Naphthalene generally is the tar having the highest concentration in the syngas. Due to naphthalene being the most prevalent tar, frequently the concentration of naphthalene in the scrubbed syngas is a viable indicator of the extent of removal of all tars from the syngas. The conditions and duration of contact during the scrubbing are sufficient to reduce the concentration of naphthalene in the syngas to less than about 5, preferably less than about 1 or 3, ppm(mole).

A number of options exist for operation of the scrubber. For instance, the aqueous medium can be recycled. A purge stream can be taken, and if necessary, fresh aqueous medium added, to maintain aqueous medium. Alternatively, the aqueous medium may be used on a once through basis. In yet another alternative, the aqueous medium is subjected to a stripping unit operation to remove tars from the aqueous medium, and the aqueous medium is recycled. The recycling of the aqueous medium may be directly to the scrubber or may be admixed with hot syngas prior to the scrubber and condensed out in the scrubber. Where the aqueous medium contains particulates removed from the syngas, the aqueous medium may be subjected to operations to remove at least a portion of the particulates such as filtration, decanting, centrifuging, and the like.

In any of these alternatives, all or a portion of the spent aqueous medium may be sent to waste water treatment. Preferably, the spent aqueous medium is subjected to a stripping unit operation whether or not the aqueous medium is recycled to the scrubber. Stripping provides several advantages. First, tars are removed from the aqueous medium thereby reducing the impact on waste water treatment if the aqueous medium is disposed. Second, the stripping gas will contain these tars and the hydrocarbon values can be, for instance, subjected to a thermal oxidation and converted to heat values. Third, stripping may reduce contaminant content of the aqueous medium sufficiently that the aqueous medium can be recycled for use in the scrubbing or used elsewhere in the process, including, but not limited to being used as make-up water for the fermentation or cooling water or other process water.

The stripping unit operation may be carried out using any suitable stripping gas, temperature pressure and equipment. The temperature of the stripping may essentially be at the same temperature as the spent aqueous medium or may be at a higher or lower temperature. In general, the stripping is at a temperature between about 15° C. to 200° C., preferably between about 60° C. and 120° C. or 150° C. Where the aqueous medium is recycled and the scrubbing unit operation also serves to cool the incoming syngas, it is desired that the aqueous medium be supplied to the stripper at a lower temperature than that used in the scrubbing unit operation. In any event, the aqueous medium recycled to the scrubbing unit operation should be at a temperature sufficiently high to assure that the sought temperature in the scrubber can be maintained. Where the syngas being passed to the scrubber is introduced using an eductor, cooler, recycled aqueous medium may be beneficially used as the motive fluid to effect a direct heat exchange.

The pressure for the stripping unit operation can vary over a wide range, and the pressure of the exiting stripping gas is usually in the range of from about 5 to 1000, say, 10 to 300, kPa absolute. The pressures used will, in part, be affected by the type of stripping equipment used. Suitable strippers include, but are not limited to, un-packed, trayed and packed columns; spargers; trickle bed contactors; stirred and agitated vessels; vortex scrubbers; venturi scrubbers; tortuous pipe, spray towers and dissolved gas flotation systems. A plurality of strippers may be used in parallel or in series to effect the sought tar reduction in a cost effective manner. The aqueous medium may be the continuous or the discontinuous phase. The contact between the stripping gas and the aqueous medium may be co-current, counter current or cross-current. Preferably, the discontinuous phase is in the form of droplets or bubbles having relatively small diameters. Often the droplets or bubbles have a diameter of less than about 5, preferably less than about 2, millimeters, preferably between about 20 and 1000, microns.

The stripping gas may be any suitable gas stream capable of removing tars from the aqueous medium. Preferred stripping gases are those existing in the process for converting carbonaceous feedstock to syngas or bioconverting syngas to oxygenated organic compound such as process off-gases or gases being passed to the gasification operations. For example, the stripping gas may be a gas fuel or an oxygen-containing gas used for a partial oxidation in a second thermal operation for the gasification of the carbonaceous feedstock, or an oxygen containing gas for oxidation of char and tars from the first thermal operation of the gasifier.

Desirably, the stripping gas will be further used in the gasification operation or will be subjected to thermal oxidation to generate heat. Preferably, the process off-gas is at least a portion of an off-gas withdrawn from the fermentation zone, most preferably after oxygenated compound has been recovered from the off-gas.

The combination of the ratio of stripping gas to aqueous medium and the duration of contact between the liquid and gas phases should be sufficient, under the conditions of the contacting, to provide a desired reduction of tar concentration in the aqueous medium. Frequently, the concentration of naphthalene in the aqueous medium is reduced by at least about 20, preferably at least about 50, and sometimes at least about 80, percent between the spent aqueous medium supplied to the stripping unit operation and the lean aqueous medium exiting the stripping unit operation.

The aqueous medium, due to the high temperature of the scrubbing, is relatively free of components, other than tar and ash, if any. In an aspect of this invention where the syngas is generated by gasification, aqueous medium, especially after stripping to remove naphthalene and ash removal, if required, is used to cool hot syngas using latent heat of vaporization. Since the aqueous medium is relatively free from components contained in the syngas, the aqueous medium can be injected directly into the hot syngas stream without resulting in a build up in the syngas of components adverse to the fermentation such as hydrogen cyanide, ethylene and acetylene. Using the latent heat of vaporization of water, the syngas stream can be rapidly cooled. This rapid cooling is particularly beneficial to quench the syngas from the gasification to mitigate continuation of chemical reactions that can occur at the elevated temperature of the gasification.

Ammonia Removal and Recovery

Ammonia is removed from the scrubbed syngas by contact with a second aqueous medium (aqueous medium of step (b)) capable of absorbing ammonia at a temperature at which ammonium bicarbonate is thermally stable often at a temperature between about 20° C. and 70° C. or 80, say, 25° C. to 60° C. By removing tars, ammonia can be effectively removed by the second aqueous medium from the syngas without undue contamination of other components in the syngas. Accordingly, the second aqueous medium containing recovered ammonia can in some instances be used without further treatment as a nutrient for the fermentation.

The cooling of the scrubbed syngas can be accomplished by any suitable means including, but not limited to, one or more of indirect heat exchange prior to the contact with the aqueous medium providing an aqueous condensate and direct heat exchange by contact with the second aqueous medium. The cooling of the scrubbed syngas, which is substantially saturated with water at the exit temperature from the prior scrubbing, will result in the condensation of water. The condensed water will be substantially devoid of molecular oxygen or reactive oxygen, tars and ash, and thus is desirable for use as make-up water to the fermentation operation. In some instances, essentially all of the make-up water for the fermentation can be supplied by the condensate.

Both ammonia and carbon dioxide are absorbed by the aqueous medium and cause ammonium bicarbonate to be formed. The pressure for the ammonia recovery unit operation can vary over a wide range and the pressure of the syngas after the ammonia recovery unit operation is frequently in the range of between about 5 to 1000, say, 10 to 300, kPa absolute. Lower syngas exit pressures are generally preferred to avoid undue sorption of hydrogen cyanide, e.g., in the range of 10 to 150 or 200 kPa absolute. The pressures used will, in part, be affected by the type of contacting equipment used.

The aqueous medium for contact with the scrubbed syngas (aqueous medium of step (b)) comprises water and one or more adjuvants can be added to the water. Typically, suitable absorption of ammonia can be achieved without using adjuvants. The source of the water may be fresh water, a used process water stream or, preferably, condensate from the syngas. Where water is condensed from the syngas during the contact with the second aqueous medium, a purge stream maintains constant volume at steady state. Frequently, no additional water need be added, and thus the composition of the aqueous medium is defined by the steady state operating conditions. Often, the aqueous medium used for ammonia recovery is maintained at a pH less than about 6.5, say, between about 4.5 or 5 and 6.

Suitable contact equipment include, but are not limited to, un-packed, trayed and packed columns; spargers; trickle bed contactors; stirred and agitated vessels; vortex scrubbers; venturi scrubbers; tortuous pipe and spray towers. A plurality of contactors may be used in parallel or in series to effect the sought ammonia recovery in a cost effective manner. The aqueous medium may be the continuous or preferably the discontinuous phase. The contact between the syngas and the aqueous medium may be co-current, counter current or cross-current. The discontinuous phase is preferably in the form of droplets or bubbles. Often the droplets or bubbles have a diameter of less than about 5, preferably less than about 2, millimeters, preferably between about 20 and 1000, microns.

The duration of the contact between the syngas and the aqueous medium is sufficient to achieve the desired recovery of ammonia. Preferably at least about 70, and more preferably at least about 90, percent of the ammonia in the syngas is recovered. Often the syngas after removal of ammonia has an ammonia content of less than about 100, preferably between about 0.1 and 75, ppm(mole). The duration of the contacting is generally between about 2 and 120, say, 5 and 40, seconds.

The aqueous medium can be used on a once through basis or may be recycled after contacting the syngas to effecting the removal of ammonia to achieve a higher ammonium bicarbonate content at steady state. The concentration of ammonium bicarbonate in the ammonium bicarbonate-laden aqueous medium thus can vary widely. Often the ammonium bicarbonate-laden aqueous medium contains from about 0.01 to 10 mass percent ammonium bicarbonate, and where the aqueous medium is recycled, the ammonium bicarbonate content is frequently in the range of about 1 to 5 mass percent. The rate of purge of the aqueous medium can also be used to control the amount of hydrogen cyanide contained in the aqueous medium.

At least a portion (aliquot or fraction), say, between about 70 and 100 percent, frequently at least about 90 percent to substantially all, the aqueous medium withdrawn from the contacting with the second aqueous medium, is passed to the fermentation operation. The second aqueous medium may be used on a once-through basis or recycled with a purge providing the aqueous medium containing ammonium bicarbonate to be supplied to the fermentation operation. The mass flow ratio of purge to recirculating aqueous medium is at least sufficient to compensate for any water recovered from the syngas to maintain a constant volume of aqueous medium. Generally, the mass flow ratio is determined by the sought concentration of ammonium bicarbonate in the aqueous medium. If the water condensed from the syngas is not sufficient to provide a constant volume of aqueous medium, additional water is added.

By selecting the conditions for the scrubbing unit operation and for the ammonia recovery unit operation, the amount of water condensed during the operation to recover ammonia can be controlled. Often the temperatures and pressures of the scrubbing unit operation and the ammonia recovery unit operation are such that at least about 10, preferably at least about 15, often 15 to 30 or 40, percent of the water need for the fermentation is provided by the ammonia recovery unit operation, and between about 50 to 100 percent of that amount is derived from condensate from the syngas.

Preferably the ammonia recovery unit operation is operated such that little, if any, methane, ethylene, acetylene, benzene, toluene, and xylene are sorbed by the aqueous medium. Some hydrogen sulfide and carbonyl sulfide may be sorbed by the aqueous medium. These sulfur-containing components are useful nutrients for the fermentation. However, as conditions are used that favor greater amounts of hydrogen sulfide and carbonyl sulfide sorption, the sorption of hydrogen cyanide also increases. Thus, where no further treatment of the ammonium bicarbonate-containing aqueous medium is desired prior to its being introduced into the fermentation zone, the concentration of hydrogen sulfide and carbonyl sulfide in the aqueous medium is relatively low, say, between about 1 and 25 ppm(mole). The aqueous medium, in addition to ammonium bicarbonate, may contain a minor amount of nitrates and nitrites from nitrogen oxides contained in the syngas.

Where the hydrogen cyanide concentration in the ammonium bicarbonate-containing aqueous medium is greater than desired, the aqueous medium may be subjected to treatment to eliminate at least a portion of the hydrogen cyanide. Preferably the treatment is at least one of hydroxyl radical oxidation treatment, adsorption, absorption and biological treatment that does not oxidize or absorb ammonium cation. Frequently it is desired to reduce the hydrogen cyanide concentration in the aqueous medium being passed to the fermentation operation to less than about 0.5, more preferably less than about 0.1, ppm(mass).

Optional Cleanup of the Syngas

Subsequent to the recovery of ammonia, in some instances additional cleanup of the syngas may be desired. The additional cleanup may be desired because of the sensitivity of the particular microorganisms used for the anaerobic fermentation to the residual amounts of one or more of the components in the syngas. Where the operation of the partial oxidation is primarily sought to lower the concentration of components sought to be removed as opposed to reducing them to levels tolerable in the fermentation, additional cleanup will be required. As stated above, the lowering of the concentration of these components facilitates the removal of these components in subsequent cleanup operations. More importantly, even with wide variations in concentrations of these components in the crude syngas, the variations in concentration of the syngas after partial oxidation are attenuated. Hence the equipment design and control systems need not address the wide variations.

One optional cleanup operation is water scrubbing. Hydrogen cyanide can be removed by water scrubbing or by scrubbing in the presence of a reactant. See, for instance, United States Published Patent Application No. 20110097701 A1, hereby incorporated by reference in its entirety. The water scrubbing also serves to remove at least a portion of remaining impurities from the syngas such as ethylene, acetylene, ammonia, hydrogen sulfide and carbonyl sulfide. The scrubbing may be conducted in any convenient manner. Often, the temperature of the scrubbing is in the range of about 4° C. to 50° C., and the scrubbing is often conducted at superatmospheric pressure, e.g., frequently at about 105 to 1000 KPa absolute. Water pressure swing absorption can be used if desired. The pH of the scrubbing solution is usually maintained in the range of about 5.5 to 8, preferably between about 6 to 6.5. Reactants for hydrogen cyanide can be advantageous in that hydrogen cyanide can be converted to less toxic compounds. Aldehydes are particularly preferred reactants due to their availability. Examples of aldehydes include, but are not limited to, formaldehyde, acetaldehyde, and acrolein(prop-2-enal) with formaldehyde being most preferred.

Another optional cleanup operation uses physical solvents such as glycols, e.g., triethylene glycol, and alkyl ethers of polyethylene glycols such as dimethyl ethers. Another optional cleanup operation is chemical oxidation with one or more peroxygenated reactants, preferably permanganate such as sodium permanganate and potassium permanganate. The chemical oxidation is particularly effective in reducing the concentration of compounds that have ethylenic and acetylenic unsaturation and reducing the concentration of nitric oxide and sulfur compounds. The chemical oxidation may be conducted using the peroxygenated reactant in an aqueous solution. Often, the temperature of the chemical oxidation is in the range of about 4° C. to 50° C., and the chemical oxidation may be conducted at subatmospheric, atmospheric or superatmospheric pressure, e.g., frequently at about 105 to 1000 KPa absolute. The pH of the chemical oxidation solution is usually maintained in the range of about 5.5 to 8, preferably between about 6 to 6.5.

Another cleanup operation uses chemical scavengers such as sodium hydroxide, nitric acid, sodium hypochlorite and the like in an aqueous scrubbing solution to remove one or more components from the syngas. If a chemical oxidation is used, this type of cleanup operation is usually unnecessary.

Carbon dioxide can be removed from the syngas. In most instances, the concentration of carbon dioxide in the partially-oxidized syngas is sufficiently low that a carbon dioxide removal operation is not necessary to achieve acceptable fermentation performance. However, if off gases from the fermentation are recycled, it is possible that undesirable carbon dioxide build-up could occur. In such instances, a carbon dioxide removal step could be justified during the cleanup of the syngas especially where no carbon dioxide is being removed from the recycling off gases. Any suitable carbon dioxide removal process may be used including amine extraction, alkaline salt extractions, water absorption, membrane separation, adsorptions/desorption, and physical absorption in organic solvents. A preferred process for removal of carbon dioxide from gases is by contacting the gas with an aqueous solution containing oxygenated organic compound. This process is disclosed in U.S. Patent application No. 2008/0305539, filed Jul. 23, 2007, herein incorporated by reference in its entirety. See also, U.S. patent application Ser. No. 12/826,991, filed Jun. 30, 2010 herein incorporated by reference in its entirety, which discloses contacting a gas stream with a mixture of water and a surface active agent under pressure to sorb carbon dioxide and phase separating the gas and liquid stream to provide a gas stream with reduced carbon dioxide concentration to be used as feed to a reactor.

Another optional cleanup operation comprises contacting the syngas with aqueous fermentation medium containing microorganisms being discharged from the fermentation operation, said contacting being under anaerobic fermentation conditions. Components such as hydrogen cyanide and acetylene that are absorbed by the microorganism but are not released or not readily released can thus be removed with the microorganisms from the syngas prior to being introduced into the fermentation operation. The contacting may be by any suitable manner provided that sufficient residence time of the gas phase exists for mass transfer of the components sought to be removed to the aqueous phase. Apparatus such as bubble column reactors; jet loop reactors; stirred tank reactors; trickle bed reactors; biofilm reactors; and static mixer reactors including, but not limited to, pipe reactors may find application for this cleanup operation. Oxygenated organic compound is usually produced and can be recovered from the aqueous phase. A discussion of pre-reactors is provided in copending U.S. patent application Ser. No. 13/243,347, filed on Sep. 23, 2011, hereby incorporated in its entirety by reference.

Fermentation Gas Feed

The cleaned syngas serves as fresh gas feed to the fermentation operation. The cleaned syngas may be admixed with other gases, including but not limited to, syngas from other sources and recycled off gas from the fermentation. The syngas from other sources may include, but is not limited to, syngas from another biomass gasifier, syngas made from other sources of hydrocarbon such as natural gas, gas generated by reforming or partial oxidation of hydrocarbon-containing materials, and gas generated during petroleum and petrochemical processing. Thus, the gas feed to a fermentor may have the same or a different composition as the composition of the cleaned syngas. The composition of the syngas generated from biomass may be processed to provide a composition which, when admixed with the gases from the other sources, is suitable for a gas feed to the fermentation operation. The Component Composition of typical cleaned syngas is set forth in Table I.

TABLE I

| Component | Minimum | Maximum | Preferred Minimum | Preferred Maximum |
|---|---|---|---|---|
| Carbon Monoxide, mole % | 25 | 70 | 40 | 65 |
| Hydrogen, mole % | 30 | 70 | 40 | 65 |
| Carbon Dioxide, mole % | 1 | 20 | 3 | 15 |
| Methane, mole % | 0.1 | 1 | 0.1 | 0.75 |
| Acetylene, ppm (mole) | 0.01 | 10 | 0.1 | 5 |
| Ethylene, ppm (mole) | 0.1 | 50 | 0.5 | 10 |
| Benzene, ppm (mole) | 0.001 | 30 | 0.05 | 10 |
| Tars, naphthalene, ppm (mole) | 0.001 | 10 | 0.001 | 5 |
| Hydrogen sulfide, ppm (mole) | 0.01 | 30 | 0.05 | 20 |
| Carbonyl sulfide, ppm (mole) | 0.01 | 25 | 0.05 | 15 |
| Ammonia, ppm (mole) | 0.01 | 100 | 0.1 | 75 |
| Nitric oxide, ppm (mole) | 0.5 | 100 | 0.5 | 50 |
| Hydrogen cyanide, ppm (mole) | 0.001 | 2 | 0.001 | 0.3 |
| Other, ppm (mole) | 20 | 10000 | 20 | 10000 |

(Excluding nitrogen and water)

(Excluding nitrogen and water)

Oxygenated Compound, Microorganisms and Fermentation Conditions:

The oxygenated organic compounds produced in the processes of this invention will depend upon the microorganism used for the fermentation and the conditions of the fermentation. One or more microorganisms may be used in the fermentation menstruum to produce the sought oxygenated organic compound. Bioconversions of CO and $H_2/CO_2$ to acetic acid, propanol, butanol, butyric acid, ethanol and other products are well known. For example, in a recent book concise description of biochemical pathways and energetics of such bioconversions have been summarized by Das, A. and L. G. Ljungdahl, *Electron Transport System in Acetogens* and by Drake, H. L. and K. Kusel, *Diverse Physiologic Potential of Acetogens*, appearing respectively as Chapters 14 and 13 of Biochemistry and Physiology of Anaerobic Bacteria, L. G. Ljungdahl eds., Springer (2003). Any suitable microorganisms that have the ability to convert the syngas components: CO, $H_2$, $CO_2$ individually or in combination with each other or with other components that are typically present in syngas may be utilized. Suitable microorganisms and/or growth conditions may include those disclosed in U.S. patent application Ser. No. 11/441,392, filed May 25, 2006, entitled "Indirect Or Direct Fermentation of Biomass to Fuel Alcohol," which discloses a biologically pure culture of the microorganism *Clostridium carboxidivorans* having all of the identifying characteristics of ATCC no. BAA-624; U.S. Pat. No. 7,704,723 entitled "Isolation and Characterization of Novel Clostridial Species," which discloses a biologically pure culture of the microorganism *Clostridium ragsdalei* having all of the identifying characteristics of ATCC No. BAA-622; both of which are incorporated herein by reference in their entirety. *Clostridium carboxidivorans* may be used, for example, to ferment syngas to ethanol and/or n-butanol. *Clostridium ragsdalei* may be used, for example, to ferment syngas to ethanol.

Suitable microorganisms and growth conditions include the anaerobic bacteria *Butyribacterium methylotrophicum*, having the identifying characteristics of ATCC 33266 which can be adapted to CO and used and this will enable the production of n-butanol as well as butyric acid as taught in the references: "Evidence for Production of n-Butanol from Carbon Monoxide by *Butyribacterium methylotrophicum*," Journal of Fermentation and Bioengineering, vol. 72, 1991, p. 58-60; "Production of butanol and ethanol from synthesis gas via fermentation," FUEL, vol. 70, May 1991, p. 615-619. Other suitable microorganisms include: *Clostridium Ljungdahlii*, with strains having the identifying characteristics of ATCC 49587 (U.S. Pat. No. 5,173,429) and ATCC 55988 and 55989 (U.S. Pat. No. 6,136,577) that will enable the production of ethanol as well as acetic acid; *Clostridium autoethanogenum* sp. nov., an anaerobic bacterium that produces ethanol from carbon monoxide. Jamal Abrini, Henry Naveau, Edomond-Jacques Nyns, Arch Microbiol., 1994, 345-351; Archives of Microbiology 1994, 161: 345-351; and *Clostridium Coskatii* having the identifying characteristics of ATCC No. PTA-10522 filed as U.S. Ser. No. 12/272,320 on Mar. 19, 2010. All of these references are incorporated herein in their entirety.

Suitable microorganisms for bioconversion of syngas to oxygenated organic compound generally live and grow under anaerobic conditions, meaning that dissolved oxygen is essentially absent from the fermentation liquid. Adjuvants to the aqueous menstruum may comprise buffering agents, trace metals, vitamins, salts etc. Adjustments in the menstruum may induce different conditions at different times such as growth and non-growth conditions which will affect the productivity of the microorganisms. U.S. Pat. No. 7,704,723, hereby incorporated by reference in its entirety, discloses the conditions and contents of suitable aqueous menstruum for bioconversion CO and $H_2/CO_2$ using anaerobic microorganisms.

Anaerobic fermentation conditions include a suitable temperature, say, between 25° and 60° C., frequently in the range of about 30° to 40° C. The conditions of fermentation, including the density of microorganisms, aqueous menstruum composition, and syngas residence time, are preferably sufficient to achieve the sought conversion efficiency of hydrogen and carbon monoxide and will vary depending upon the design of the fermentation reactor and its operation. The pressure may be subatmospheric, atmospheric or super atmospheric, and is usually in the range of from about 90 to 1000 KPa absolute and in some instances higher pressures may be desirable for biofilm fermentation reactors. As most reactor designs, especially for commercial scale operations, provide for a significant height of aqueous menstruum for the fermentation, the pressure will vary within the fermentation reactor based upon the static head.

The fermentation conditions are preferably sufficient to effect at least about 40 or 50 percent conversion of the carbon monoxide in gas feed. For commercial operations, the fermentation operation preferably provides a total molar conversion of hydrogen and carbon monoxide in the net gas feed in the range of about 85 to 95 percent. Due to the low solubilities of carbon monoxide and hydrogen in the aqueous phase, achieving these high conversions may require one or more of using multiple fermentation reactors and recycling off gas from a reactor.

The rate of supply of the gas feed under steady state conditions to a fermentation reactor is such that the rate of transfer of carbon monoxide and hydrogen to the liquid phase matches the rate that carbon monoxide and hydrogen are bioconverted. Hence, the dissolved concentration of carbon monoxide and hydrogen in the aqueous phase remains constant, i.e., does not build-up. The rate at which carbon monoxide and hydrogen can be consumed will be affected by the nature of the microorganism, the concentration of the microorganism in the aqueous menstruum and the fermentation conditions. As the rate of transfer of carbon monoxide and hydrogen to the aqueous menstruum is a parameter for operation, conditions affecting the rate of transfer such as interfacial surface area between the gas and liquid phases and driving forces are important.

To increase the conversion of carbon monoxide and hydrogen in the fresh gas feed to the fermentation, off-gas withdrawn from a fermentation reactor may be recycled or passed to a fermentation reactor that is sequential in gas feed flow. Where off-gas is recycled, the portion of off-gas recycled is generally selected to avoid an undue build-up of the concentration of inerts and other gases in the fermentation reactor.

Fermentation Reactors

The fermentation reactors used in this invention may be of any suitable design; however, preferably the design and operation provides for a high conversion of carbon monoxide and hydrogen to oxygenated organic compound. Fermentation reactors include, but are not limited to, bubble column reactors; jet loop reactors; stirred tank reactors; trickle bed reactors; biofilm reactors; moving bed reactors; membrane reactors and static mixer reactors including, but not limited to, pipe reactors.

Product Recovery

The fermentation vessel may have added from time to time or continuously one or more streams of water, nutrients or adjuvants, and microorganisms. A portion of the aqueous menstruum is withdrawn from time to time or continuously from the reactor for product recovery. Usually, the withdrawal is made at a point at the upper portion of the aqueous menstruum in the vessel. Product recovery can consist of known equipment arrangements for removal of residual cell material, separation and recovery of liquid products from the fermentation liquid, return of recovered fermentation liquid and purging of waste streams and materials. Suitable equipment arrangements can include filters, centrifuges, cyclones, distillation columns, membrane systems and other separation equipment. US 2009/0215139 A1 shows an arrangement for a product recovery reactor that recovers an ethanol product from a bioreactor, herein incorporated by reference in its entirely.

Carbon Dioxide Removal

Carbon dioxide may be removed from at least one of the aqueous menstruum in a reactor or from the off-gas from a reactor where the off-gas is recycled or passed to a subsequent fermentation reactor. Any suitable carbon dioxide removal process may be used including amine extraction, alkaline salt extractions, water absorption, membrane separation, adsorptions/desorption, and physical absorption in organic solvents.

DRAWING

A general understanding of the invention and its application may be facilitated by reference to FIG. 1. FIG. 1 is a schematic depiction of an apparatus generally designated as 100 suitable for practicing the processes of this invention. FIG. 1 omits minor equipment such as pumps, compressors, valves, instruments and other devices the placement of which and operation thereof are well known to those practiced in chemical engineering. FIG. 1 also omits ancillary unit operations. The process and operation of FIG. 1 will be described in the context of the recovery and production of ethanol. The process is readily adaptable to making other oxygenated products such as acetic acid, butanol, propanol and acetone.

The discussion of the drawings also encompasses a description of a computer simulation of a process producing 4530 kilograms of ethanol per hour.

Conveyor line 102 provides biomass to the process for conversion to ethanol. For purposes of the discussion, the biomass is wood chips. About 20,600 kilograms per hour of wood chips having a moisture content of about 40 to 50 mass percent are supplied via line 102 to dryer 104. Dryer 104 uses direct heat exchange with hot gases from line 132 to dry the wood chips. The dried wood chips now containing about 15 to 20 mass percent water are conveyed via line 106 to the gasification unit. The gases used for the drying are exhausted from dryer 104 via line 136.

The gasification unit may be of any suitable design. For purposes of illustration herein, a gasification unit is an indirect gasification unit having (i) gasification reactor 108 in which the biomass is contacted with a recirculating, heat transfer medium (for illustration, sand) and steam, and (ii) combustion reactor 120 in which char produced in the gasification reactor is combusted and sand reheated for recycle to gasification reactor 108. In further detail, the dried wood chips are passed via line 106 to gasification reactor 108. Gasification reactor 108 contains hot sand to provide the heat for the gasification, and the sand may also provide some catalytic activity. Also steam is provided to gasification reactor 108 via line 138 for reaction with the biomass. Crude syngas exits gasification reactor 108 at a temperature between about 830° C. and 870° C. and a pressure of about 135 KPa absolute. Char and sand are also withdrawn with the crude syngas. Tars may exist on the char and the sand. Line 110 directs the effluent from gasification reactor 108 to cyclone 112.

Cyclone 112 serves to separate the solids from the crude syngas. The crude syngas passes from cyclone 112 to partial oxidation reactor 144 via line 114. The solids separated in cyclone 112 are passed via line 118 to combustion reactor 120. Air is provided via line 122 to combustion reactor 120. The air may be preheated to facilitate the combustion. Char is combusted in combustion reactor 120 to reheat the sand to a temperature of between about 1020° C. and 1100° C. The combustion gases and reheated sand are passed to cyclone 128 via line 126. The reheated sand that is separated by cyclone 128 is passed to gasification reactor 108 via line 142. The hot combustion gases and ash from cyclone 128 are exhausted via line 130 and passed to cyclone 134. Ash is removed from cyclone 134 via line 140. The hot combustion gases are exhausted from cyclone 134 through line 132 and may be used for preheating the combustion air fed to combustion reactor 120 and then for drying the biomass.

The hot, crude syngas in line 114 contains about 42 mole percent hydrogen, 25 mole percent carbon monoxide and 19 mole percent carbon dioxide. (All gas compositions set forth herein are on an anhydrous basis unless otherwise specified.)

The hot, crude syngas in line 114 is passed to partial oxidation reactor 144. Partial oxidation reactor 144 may be of any suitable design. As shown in FIG. 1, partial oxidation reactor 144 is also fed a mixture of natural gas supplied by line 146 and oxygen supplied by line 147. The mixture is formed in section 144a of partial oxidation reactor 144 under conditions such that essentially all of the natural gas is oxidized prior to the mixture combining with the hot, crude syngas. About 260 kilograms per hour of natural gas are supplied and about 2000 kilograms of oxygen are supplied. The temperature of the partial oxidation is between about 1400° C. and 1450° C. Partially-oxidized syngas exits partial oxidation reactor 144 via line 148. Water provided by line 162 is injected into the syngas exiting partial oxidation reactor to quickly reduce its temperature to about 1000° C. The partially-oxidized syngas contains about 46 mole percent hydrogen, 41 mole percent carbon monoxide, 12 mole percent carbon dioxide and 0.15 mole percent methane.

The partially oxidized syngas is directed by line 148 to waste heat recovery boiler 150. Water is provided to waste heat recovery boiler 150 by line 152 and steam at a pressure of about 1030 KPa gauge is produced and withdrawn via line 154. This steam can be used as the steam source for gasification reactor 108 and for reboiler heat for ethanol distillation and for other uses within the process. The partially-oxidized syngas is cooled to about 135° C. in waste heat recovery boiler 150 and is passed via line 155 to scrubber 156. The partially-oxidized syngas is at a pressure of about 35 KPa gauge and a temperature of about 135° C.

Scrubber 156 is a countercurrent absorption column containing structured packing. Aqueous medium is passed downwardly in scrubber 156 to contact upwardly flowing syngas. The temperature of the syngas at the top of scrubber 156 is about 105° C. Line 158 recirculates aqueous medium from the bottom to the top of scrubber 156, and a portion, a purge, of the tar laden aqueous medium is withdrawn from line 158 via line 161 and passed to stripper 157. Subsequent in flow to the point of the purge in line 158, the recirculating aqueous medium is cooled in heat exchanger 159. Make-up water, if required, can be provided via line 160 to line 158. The temperature of the recirculating aqueous medium entering the top of scrubber 156 is about 95° C. The mass flow of the recirculating aqueous medium is sufficient to cool the syngas from 135° C. to 105° C.

Stripping column 157 is operated at slightly above atmospheric pressure and about 100° C. Stripping column 157 is a packed column having tar-laden aqueous medium from line 161 passed downwardly and a stripping gas, described later, from line 232 passed upwardly. The stripping gas containing naphthalene and other heavy tars exits stripping column 157 at the top via line 165 and can be passed to a thermal oxidizer (not shown) to generate heat, e.g., for drying the biomass. A lean (tar concentration reduced) aqueous medium is withdrawn via line 162 from the bottom of stripping column 157 and is passed via line 162 to the exit of partial oxidation reactor 144 where it is injected to cool the exiting syngas. As shown, a purge is taken from line 162 by line 164 which can be passed to waste treatment.

Scrubbed syngas exits scrubber 156 via line 166 at a temperature of about 105° C. and is passed to ammonia sorption column 167. Ammonia sorption column is an unpacked, bubble column and operates at about 40° C. As shown, ammonia sorption column is operated such that water is recovered from the syngas. Thus, ammonia sorption column 167 serves the function of recovering ammonia and carbon dioxide from the syngas and also cooling the syngas.

The syngas being passed to ammonia sorption column is at low pressure and must also be cooled. Rather than compressing the syngas to permit it to be passed into the bottom of ammonia sorption column 167, the syngas is introduced via slot injectors using the aqueous medium as the motive fluid. Aqueous medium is from column 167 passes into line 168 for recirculation. Line 168 contains heat exchanger 168a to cool the aqueous medium sufficiently that ammonia sorption column 167 can operate with an exit temperature of about 40° C. Line 168b withdraws sufficient aqueous medium from line 168 after cooler 168a to provide the motive fluid for the slot injectors. The aqueous medium in line 168b also serves to effect a direct heat exchange with the entering syngas. A portion of the aqueous medium in line 168 is withdrawn via line 170 as the aqueous ammonium bicarbonate product stream. As shown, the aqueous ammonia bicarbonate product stream is subjected to a treatment in reactor 171 to reduce the concentration of cyanide anion and any ethylene or acetylene therein. For this purpose, line 172 provides a combination of ozone and hydrogen peroxide to reactor 171. Reactor 171 is further energized by ultraviolet light thereby effectively removing cyanide anion and organics. The treated aqueous ammonium bicarbonate product stream is passed via line 173 to fermentor 214 which is discussed below. Any make-up water needed for the sorption of ammonia in ammonia sorption column 167 can be provided via line 169 to line 168.

The syngas from ammonia sorption column 167 is passed via line 174 to compressor 176. The function of compressor 176 will depend upon whether the syngas is directly fed to fermentor 214 or must provide the syngas at a pressure suitable for additional cleanup operations. As shown, the syngas is directed to a water pressure swing absorption operation. Accordingly, the pressure of the syngas is increased to about 750 KPa gauge and the compressed syngas exits via line 178. Due to the increase in pressure condensate is formed and is removed from the compressed syngas through line 180.

FIG. 1 depicts the use of both a water pressure swing absorption and a permanganate oxidizer. This is for purposes of illustration. In practice neither or only one of these optional cleanup operations for the syngas would typically be used unless very high purity syngas is sought for the fermentation. Line 178 directs the syngas to absorption column 182 of the water pressure swing adsorption unit. Water at a temperature of about 7° C. is provided to the absorption column via line 184. The water, if desired, can contain other components to assist in the removal of components from the syngas such as buffers and reactants such as aldehydes, hypochlorites, peroxygenates, and the like. The spent water absorbent exits absorption column via line 186 and is passed to desorption column 188. Desorption column is operated at about atmospheric pressure and a temperature of about 7° C. Desorbed gases exit desorption column 188 via line 192. The rejuvenated water sorbent is withdrawn from desorption column via line 184 for return to absorption column 182. Make-up water is provided to desorption column 188 by line 190. A purge stream is removed from line 184 through line 194. Syngas exits absorption column 182 via line 196 and is directed to permanganate oxidizer 198.

Permanganate oxidizer contains a column of water having about 500 ppm (mass) of sodium permanganate dissolved therein and operates at a temperature of about 38° C. and pressure of about 750 KPa gauge. The water solution is recirculated via line 200. Manganese dioxide, a co-product of the oxidation, is filtered from the recirculating water solution and removed via line 204. Make-up sodium permanganate is added via line 202.

The treated syngas is withdrawn from permanganate oxidizer 198 via line 206 and directed to sacrificial reactor 208. Sacrificial reactor 208 is optional and frequently serves to mitigate the risk of any toxins to the microorganisms passing into the fermentation reactor due to an upset during the production and cleanup of the syngas. Sacrificial reactor 208 contains aqueous fermentation medium containing microorganisms being purged from the fermentation operation. Purging of microorganisms is used to retain an advantageous average cell retention time in the fermentation reactors. Sacrificial reactor is maintained under fermentation conditions, e.g., a temperature of about 38° C. and will result in the bioconversion of syngas to ethanol subject to the microorganisms not being rendered inactive or killed by a toxin. Aqueous fermentation medium is provided to sacrificial reactor 208 via line 212 and aqueous fermentation menstruum is withdrawn via line 213. Ethanol is recovered from the withdrawn fermentation medium as will be discussed later.

Syngas is withdrawn from sacrificial reactor 208 via line 210 and is used as the gas feed for anaerobic fermentation to make ethanol. The fresh feed, for purposes of illustration, contains about 51 mole percent hydrogen, 45 mole percent carbon monoxide, 3 mole percent carbon dioxide, about 0.2 mole percent methane, about 5 ppm (mole) acetylene, about 15 ppm (mole) ethylene, about 10 ppm (mole) nitric oxide, and less than 1 ppm (mole) hydrogen cyanide (all on an anhydrous basis).

Any suitable anaerobic fermentation process can be employed. For purposes of illustration, a fermentation process using sequential deep, bubble column reactors is discussed. It is also possible to use a single stage fermentation reactor system. As shown, the fresh gas feed is passed via line 210 to bubble column 214. Bubble column 214 contains aqueous fermentation menstruum at a depth of about 20 meters and is maintained at a temperature of about 38° C. The gas feed is injected at the bottom of bubble column 214 using slot injectors and aqueous menstruum as the motive fluid. The injectors provide microbubbles. Nutrients and make-up water are provided to bubble column 214 via line 216. Line 173 also provides make-up water and nutrients to bubble column 214. Aqueous menstruum is removed from bubble column 214 via line 218 for product recovery and passed to centrifuge 238. The rate of aqueous menstruum removal is sufficient to maintain an ethanol concentration in bubble column 214 at about 2.5 mass percent. About 60 percent of the hydrogen in the gas feed and 90 percent of the carbon monoxide in the gas feed are consumed in bubble reactor 214. Centrifuge 238 provides a supernatant liquor containing ethanol which is directed to the distillation operation as will be discussed later. A concentrated microorganism-containing stream is produced by centrifuge 238 and a portion is returned to bubble column 214 via line 240 and another portion containing the cells intended to be purged, is passed to line 212 for transport to sacrificial reactor 208. While only a single bubble column 214 and centrifuge 238 is depicted, it is understood that in practice multiple bubble columns 214 and centrifuges 238 will be used. Moreover, the centrifuges are typically dedicated to a single reactor to prevent cross contamination.

Off-gas is withdrawn from the top of bubble column 214 via line 220. The off-gas contains about 36 mole percent hydrogen, 8 mole percent carbon monoxide, 54 mole percent carbon dioxide, 0.5 mole percent methane, and 1 mole percent nitrogen. The off-gas is passed to carbon dioxide removal unit 222 which is a water pressure swing absorption operation and reduces the carbon dioxide concentration to about 15 to 20 mole percent and is passed to secondary bubble column 226 via a line 224. Secondary bubble column 226 contains aqueous fermentation menstruum at a depth of about 20 meters and is maintained at a temperature of about 38° C. The gas feed is injected at the bottom of secondary bubble column 226 using slot injectors and aqueous menstruum as the motive fluid. The injectors provide microbubbles. Nutrients and make-up water are provided to bubble column 226 via line 216. Aqueous menstruum is removed from bubble column 226 via line 218 for product recovery and passed to centrifuge 238. The rate of aqueous menstruum removal is sufficient to maintain an ethanol concentration in bubble column 214 at about 2.5 to 3.0 mass percent. Centrifuge 238 provides a supernatant liquor containing ethanol which is directed to the distillation operation as will be discussed later. A concentrated microorganism-containing stream is produced by centrifuge 238 and a portion is returned to bubble column 226 via line 240 and another portion containing the cells intended to be purged, is passed to line 212 for transport to sacrificial reactor 208. While only a single centrifuge 238 is depicted, it is understood that in practice multiple centrifuges 238 will be used. Moreover, the centrifuges are typically dedicated to a single reactor to prevent cross contamination.

The off-gas from secondary bubble column 226 is passed by line 228 to tail gas scrubber 230 for removal of ethanol. Tail gas scrubber 230 uses the supernatant distillation bottoms from the distillation operation provided by line 234 to remove the ethanol. The treated gas exits tail gas scrubber via line 232 and is passed to stripper column 157 as described above. The spent distillation bottoms in tail gas scrubber 230 is withdrawn via line 236 and returned to secondary bubble column 226.

Returning to sacrificial reactor 208, the withdrawn aqueous fermentation medium is passed via line 213 to centrifuge 244. The supernatant liquid is passed from centrifuge 244 via line 246 to line 242 which transports the supernatant liquor from centrifuge 238 to the distillation operation. The solids are removed from centrifuge 244 via line 248 and passed to waste treatment.

Line 242 carries the combined supernatant liquors to distillation column 250 for ethanol recovery. Ethanol (about 92 to 94 weight percent) is recovered at the top of column 250 and is directed via line 252 to product storage or additional operation such as molecular sieve treatment and denaturing for a salable product. About 900 kilograms of distillate are produced per hour.

Distillate bottoms are removed from distillation column 250 by line 254 which directs them to hydrocyclone 256. The supernatant liquid from hydrocyclone 256 is passed via line 234 to tail gas scrubber 230. The solids are removed from hydrocyclone 256 via line 258.

It is claimed:

1. A process for generating a syngas comprising:
   (a) continuously gasifying carbonaceous feedstock at a temperature in excess of about 1000° C. to provide a syngas stream containing hydrogen sulfide, carbonyl sulfide, methane, ethylene, acetylene, benzene, toluene, xylene, tars including naphthalene, ammonia, and hydrogen cyanide;
   (b) cooling the syngas stream to a temperature below the temperature at which uncatalyzed water gas shift reactions occur;
   (c) scrubbing the syngas, said scrubbing by contact with a first aqueous medium at a temperature that is a sufficiently high temperature such that less than 40 percent of the ammonia contained in the syngas is absorbed by the aqueous medium and a pressure sufficient to provide aqueous medium in the liquid phase to provide a scrubbed syngas and an aqueous medium containing tars, wherein the contacting is for a duration sufficient such that the scrubbed syngas contains less than about 5 ppm(mole) naphthalene;
   (d) contacting the aqueous medium containing tars with stripping gas under stripping conditions sufficient to remove tars from the aqueous medium and provide a lean aqueous medium containing tars and a gas containing tars; and
   (e) introducing at least a portion of the lean aqueous medium into the syngas stream of step (b) to cool the syngas by latent heat of vaporization.

2. The process of claim 1 wherein the temperature of the syngas stream is reduced to less than about 1000° C.

3. The process of claim 1 wherein the carbonaceous feedstock is at least one of gasification of biomass, coke oven gas, petroleum refining off-gas, and steel mill waste gas.

4. The process of claim 1 wherein less than 20 percent of the ammonia contained in the syngas is absorbed by the first aqueous medium.

5. The process of claim 1 wherein at least a portion of the lean aqueous medium containing tars is purged to water waste treatment.

6. The process of claim 1 wherein the lean aqueous medium containing tars contains less than about 1 ppm (mass) naphthalene.

7. The process of claim 1 wherein the gas containing tars is thermally oxidized to provide heat.

8. The process of claim 1 wherein the temperature of the scrubbed syngas from step (c) is between about 70° C. and 100° C.

9. The process of claim 1 wherein the scrubbed syngas is contacted with a second aqueous medium capable of absorbing ammonia at a temperature at which ammonium bicarbonate is thermally stable to remove at least a portion of the carbon dioxide and ammonia from the scrubbed syngas to provide an ammonia-reduced syngas and an ammonium bicarbonate-containing aqueous medium.

10. The process of claim 9 wherein at least a portion of the ammonium bicarbonate-containing aqueous medium is treated to reduce hydrogen cyanide concentration.

11. The process of claim 10 wherein the treatment to reduce hydrogen cyanide concentration is at least one of hydroxyl radical oxidation treatment, adsorption, physical absorption and biological treatment that does not oxidize or absorb ammonium cation.

12. The process of claim 10 wherein the treatment reduces the concentration of hydrogen cyanide in the ammonium bicarbonate-containing aqueous medium to less than about 0.5 ppm(mass).

* * * * *